United States Patent [19]

Yin

[11] 4,142,101
[45] Feb. 27, 1979

[54] LOW INTENSITY X-RAY AND GAMMA-RAY IMAGING DEVICE

[75] Inventor: Lo I Yin, Silver Spring, Md.

[73] Assignee: The United States of America as represented by the Administrator of the National Aeronautics and Space Administration, Washington, D.C.

[21] Appl. No.: 817,415

[22] Filed: Jul. 20, 1977

[51] Int. Cl.$^2$ ............................................. G01J 1/58
[52] U.S. Cl. .................................. 250/363 R; 250/483
[58] Field of Search .................. 250/361 R, 363, 369, 250/483, 487, 213 VT, 330

[56] References Cited

U.S. PATENT DOCUMENTS

| | | | |
|---|---|---|---|
| 3,462,601 | 8/1969 | Sternglass | 250/369 |
| 3,749,920 | 7/1973 | Sheldon | 250/213 VT |
| 3,803,407 | 4/1974 | Anderson | 250/213 VT |

Primary Examiner—Davis L. Willis
Attorney, Agent, or Firm—Ronald F. Sandler; John R. Manning; John O. Tresansky

[57] ABSTRACT

A radiation to visible light converter is combined with a visible light intensifier. The converter is a phosphor or scintillator material which is modified to block ambient light. The intensifier includes fiber optics input and output face plates with a photocathode-microchannel plate amplifier-phosphor combination. Incoming radiation is converted to visible light by the converter which is piped into the intensifier by the input fiber optics face plate. The photocathode converts the visible light to electrons which are amplified by a microchannel plate amplifier. The electrons are converted back to light by a phosphor layer and piped out for viewing by the output fiber optics face plate. The converter-intensifier combination may be further combined with it's own radiation source or used with an independent source.

37 Claims, 5 Drawing Figures

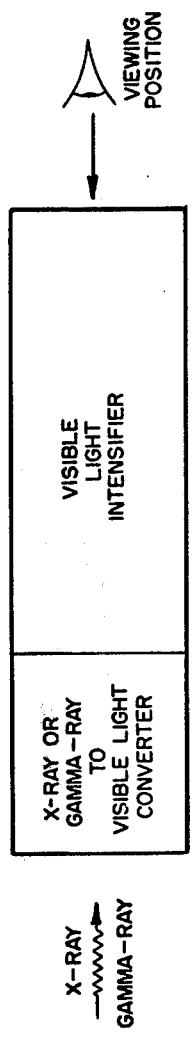
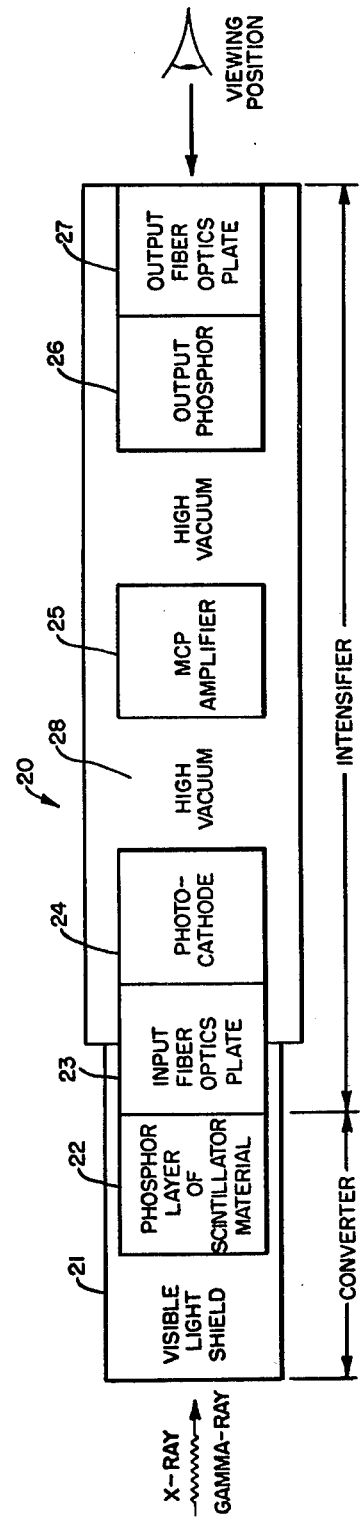

LOW INTENSITY X-RAY AND GAMMA-RAY IMAGING DEVICE

ORIGIN OF THE INVENTION

The invention described herein was made by an employee of the United States Government and may be manufactured and used by or for the Government for governmental purposes without the payment of any royalties thereon or therefore.

BACKGROUND OF THE INVENTION

The invention relates to a device for converting X-rays and gamma-rays to visible light. More particularly, this invention relates to an improved imaging device and method for converting low intensity X-rays and gamma-rays to visible light images capable of being viewed in a clinical or similar environment.

One of the great concerns in the use of X-ray and gamma-ray medical diagnosis is the biological damage produced by the high intensity flux required to achieve a good image in medical radiology. Even outside of medical applications; e.g., industrial and surveillance applications, high dosage requirements cause environmental and health problems. High dosage operational requirements are the limiting factor in the application of the computer assisted tomography (CAT) scanner and the use of fluoroscopes. In dental applications where X-ray exposures are most routine, sensitive organs, such as the thyroid and pituitary glands, are often accidentally and unnecessarily exposed to large doses of radiation from the presently utilized exta-oral X-ray machines which are not area selective. Current attempts toward alleviating high dosage requirements essentially consist of the following devices and approaches.

Various intensifying screens, films and combinations of these have been employed to reduce high dosage requirements. Rare-earth phosphor screens such as terbium activated gadolinium and lanthanum oxysulfide have high absorption efficiencies in the area of 60% at the typical medical X-ray energies of from 20 to 60 KeV. They also have high efficiencies in the subsequent conversion of the absorbed X-ray energy into large numbers of visible light photons. Proper coupling of the screens with films of high sensitivity in the band of the emitted visible light can be used to reduce the necessary exposure time by a factor of approximately 50 compared with the direct X-ray exposure of the film. However, for fluoroscopic examinations the screen alone is employed without film. In such cases, even dark-adapted eyes have difficulty distinguishing image details at normal X-ray doses. This factor, together with the required long exposure period, makes the radiation dosage unacceptably high.

Image intensifiers have also played a part in the quest to reduce required radiation dosages. X-ray image intensification began with a diode-type intensifier tube. In such a tube, kinetic energies in the order of tens of KeV are imparted to the photoelectrons generated either directly by X-rays or via X-visible-photocathode conversion before they impinge upon an output phosphor screen. Simultaneously, the electron image is also demagnified several times prior to arriving at the output screen. The demagnification in tandem with high photoelectron kinetic energies results in an intensified X-ray image. In these tubes, after the initial photoelectron generation, the number of electrons in the electron image remains constant, and is not multiplied. The electrical and electro-optical requirements of systems employing these tubes make the systems large, complex and cumbersome.

Recently, micro-channel plate (MCP) multipliers have been used directly as a photocathode for incident X-rays along with an output phosphor screen. The disadvantage of this approach is that the low probability of photoelectron production in MCP material at medical X-ray energies and the low probability of those photoelectrons that are produced deep in the material emerging and being multiplied, results in a quantum efficiency which is at most, a few percent. With such low efficiency there is loss of a great deal of information which can not be retrieved at later stages. Furthermore, X-rays which penetrate more than one channel before detection cause image degradation and loss of resolution.

In a second recent approach employing an MCP multiplier, visible light photocathode material is deposited directly on the back of an X-ray phosphor. The MCP multiplier follows the photocathode with its output phosphor. Incoming X-rays are first converted to visible light, the visible light is converted to photoelectrons, the electrons are amplified by the MCP multiplier and converted to visible light once again by the output phosphor. This second approach employing an MCP multiplier has a much higher quantum efficiency than the previously noted approach. The higher efficiency can be directly attributed to the employment of the X-ray phosphor which is highly efficient. However, the second approach exhibits an inherent problem. The proximity of the X-ray phosphor and the highly sensitive visible-light photocathode, required in the same vacuum envelope to preserve resolution, causes contamination of the photocathode material and severely limits the useful life of the intensifier. Most importantly, with both the foregoing approaches employing an MCP multiplier, X-rays must first enter the vacuum envelope of the intensifier before they are detected and intensified. Therefore, the X-rays must pass through a window material which seals the vacuum chamber. In order to prevent significant loss of quantum efficiency this window material must be very thin so that it is highly transparent to incident X-rays. On the other hand, it must also be thick enough to withstand a pressure differential of at least one atmosphere. These two basically conflicting requirements result in design compromises such as a curved window with a thickness in the order of a few hundred $\mu m$ which will, even at such minimal thicknessses, result in the loss of from 20% to 30% of the incident X-rays. Even so, while such thin windows may be adequate for the purposes of laboratory experimentation, they are generally too fragile for operation use.

OBJECTS OF THE INVENTION

Accordingly, it is an object of the present invention to provide an improved device for converting X-ray and gamma-ray radiation to visible light and intensifying the visible light.

Another object is to provide an improved X-ray and gamma-ray imaging device capable of operating at very low input radiation doses.

A further object of this invention is to provide an improved X-ray and gamma-ray imaging device which is capable of being made relatively small, lightweight, portable, inexpensive and battery operated.

Yet another object is to provide an improved X-ray and gamma-ray imaging device which is safe for handling during operation.

Still another object is to provide an improved method of X-ray and gamma-ray imaging.

These and other objects of the present invention will become apparent with reference to the following summary of the invention and the description of the preferred embodiments thereof.

SUMMARY OF THE INVENTION

According to the present invention, an X-ray and gamma-ray imaging device is provided which is capable of imaging either structure interposed between a low intensity X-ray or gamma-ray source and the device or the spatial distribution of the source itself. The imaging device includes apparatus capable of converting charged or neutral particals, as well as X-rays or gamma-rays to visible light and, thereafter, substantially intensifying the visible light to a level suitable for viewing in a clinical or other similar operational evironment. The converter serves as the front end of the device and consists of a layer of luminescent material capable of converting X-rays or gamma-rays to visible light. The converter is light coupled to a visible light intensifier which may include a microchannel plate amplifier. The radiation to visible light-visible light intensifier combination may be further combined with its own radiation source or it may be used with an independent radiation source.

BRIEF DESCRIPTION OF THE INVENTION

FIG. 1 is a block diagram of the present invention depicting the basic system concept upon which the invention is based.

FIG. 2 is a block diagrammatic view depicting the functional elements of the present invention.

DETAILED DESCRIPTION OF THE PREFERRED EMBODIMENTS

Figure 3:
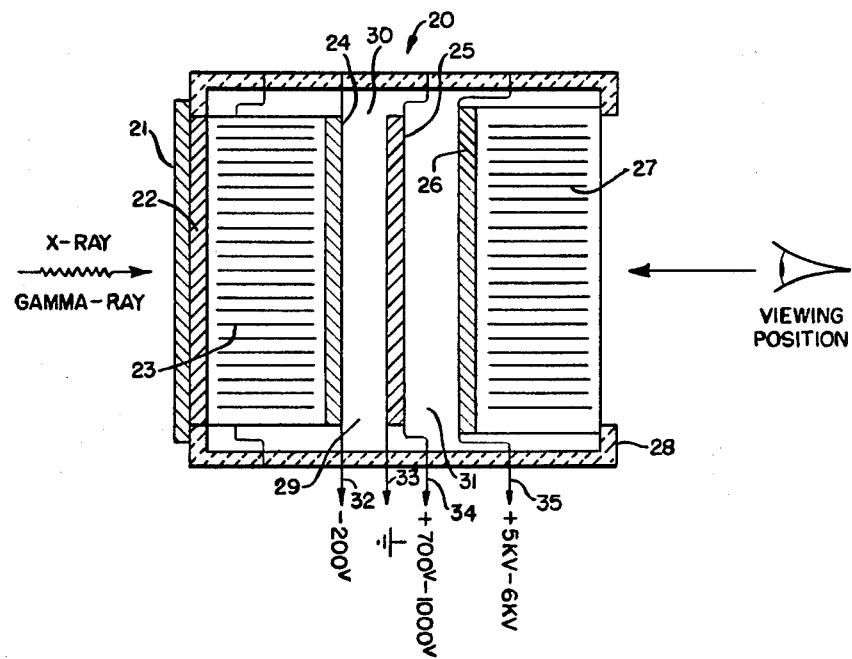
FIG. 3 is a cross-sectional view of the present invention taken along the major axis of an embodiment.

Referring to the drawing wherein reference numerals identify like parts throughout the several views, FIG. 1 depicts the fundamental X and gamma-ray to visible light intensifier system which illustrates the underlying concept upon which the low intensity X-ray and gamma-ray imaging device is based. The system may be viewed as essentially composed of a converter for converting X-rays and gamma-rays to visible light which, in turn, drives a visible light intensifier. One version can be simply a rare-earth phosphor screen, which acts as a converter and is blocked for ambient light, in contact with the face plate of an existing night-vision, visible light image intensifier tube without its optics. This version may be designated as a LIXIscope (Low Intensity X-ray Image Scope).

FIG. 2 shows the major functional elements of the overall combination of an embodiment 20 of the invention. A visible light shield 21 functions to block ambient visible light while providing virtually no shielding for X-rays or gamma-rays. The X-rays or gamma-rays which impinge on the shield 21 pass through and strike the phosphor layer or scintillator material 22 which, in turn, generates visible light. Elements 21 and 22, therefore, constitute the X-ray or gamma-ray to visible light converter. An input fiber optics plate 23 prevents lateral spread of the incoming light from element 22 and transmits the light to a photocathode 24. The photocathode converts the light transmitted thereto to electrons which, in turn, are amplified by the MCP amplifier 25. The electron output of the amplifier is thereafter converted back to visible light by an output phosphor 26. The light generated by the output phosphor is transmitted to the viewer by an output fiber optics plate 27 which is used to prevent lateral spread of the light.

FIG. 3 is a detailed cross-sectional diagram of the invention 20, previously described functionally in FIG. 2, which is taken along its major axis. The elements 23 to 27 are contained within a housing 28 which may be round and formed of any compatible ceramic, glass or other insulating material suitable for electrical insulation and vacuum isolation. The incoming radiation impinges on the light shield 21. This shield can be a thin aluminum or magnesium foil or equivalent low-Z opaque material suitable for blocking ambient visible light while being highly transparent to X-rays and gamma-rays. Alternatively, the light shield may be black plastic tape or pin-hole free paper. It must completely cover element 22.

The element 22 converts each absorbed incoming radiation particle to a large number of visible light photons. Therefore, as long as any radiation is absorbed by the converter there is little probability of information being lost. Rare earth phosphors such as terbruim activated 90% gadolinuim and 10% lanthanum oxysulfide may be employed for X-ray conversion with high efficiency. For gamma-ray conversion scintillator materials may be used, such as sodium iodide (NaI) or Cesium iodide (CsI) with or without impurity activation such as thalium (TI) or sodium (Na). In the case of the phosphor, it may be deposited directly on the fiber optics face plate 23 or deposited on a separate fiber optics plate which is then coupled to the face plate 23 while in the case of the scintillator material, it may be in the form of thin slabs which are optically coupled with the input fiber optics face plate 23. For dosimetry studies, where the incident radiation may be electromagnetic (i.e., X-ray or gamma-ray), charged, or neutral particles, plastic scintillators may be used as converters because of their tissue-equivalent properties. It should be recognized that the shield 21 may be provided by "aluminizing" element 22, which, in turn, must cover the input fiber optics face plate 23. The visible light image from the element 22 is piped into the high vacuum chamber 29 by the input fiber optics face plate 23 which is comprised of 5 μm diameter fibers. The fiber sizes should be small enough so that system resolution degradation is minimal. The plate thickness is not critical, but the ability to employ a thick plate without affecting operating characteristics gives the capability of a rugged device. Loss of resolution is typically minimal due to the close coupling between the input fiber optics face plate and the converter.

On the back face, i.e. vacuum side, of the input fiber optics face plate 23 is deposited a visible light photocathode 24 whose material, for instance, S-20 is chosen to closely match the output wave length of the element 22. Each incident radiation particle, therefore, is converted to a large number of photoelectrons by the photocathode. The photo-electrons are accelerated by approximately 200 V across a 0.2 mm gap 30 to the input of the micro-channel plate (MCP) amplifier 25 which is constructed, in this case, with 12 μm inside diameter channels and a length to diameter ratio of approximately 40. Because of the close proximity between the photocathode 24 and the input side of the micro-channel plate amplifier 25 and the high electric field ($10^4$V/cm) experienced by the electrons, loss of resolution is again made minimal.

To achieve low noise operation and to prevent the contamination of the photocathode, the large surface area of the MCP amplifier 25 with its millions of channels is thoroughly outgassed prior to sealing the intensifier portion in a high vacuum of approximately $10^{-9}$ torr. After the intensifier is sealed, it is used only as an integral unit.

The MCP amplifier 25 is operated with 700 to 1000 V in the unsaturated mode with an average electron gain of roughly $10^3$. It should be understood that when operating in the unsaturated mode with single electron inputs the MCP amplifier with straight channels has a gain distribution which is almost exponential in form. This kind of a gain distribution contributes to the noise factor of the resulting image. However, where the inputs consist of large numbers of electrons, as is the case with the LIXIscope operation, the gain distribution tends to peak toward an average value, thus improving the quality of the image. Furthermore, because each X-ray or gamma-ray generates a large number of photoelectrons, the probability of information loss is almost zero after the initial absorption in the converter.

Instead of a basic MCP amplifier, MCP amplifier 25 may be a double MCP amplifier in a "chevron" configuration or a single MCP amplifier of large length-to-diameter ratios with curved channels, both of which increase electron gains to between $10^6$ and $10^7$ with highly peaked gain distributions without ion feedback. Furthermore, the MCP amplifier, or amplifiers, employed may have increased diameters or have channels with conical inputs to cut down the inactive areas presently caused by the thickness of the channel walls.

The output electrons of the MCP amplifier 25 are accelerated by an approximate 5 to 6 KV potential across a 1.3 mm gap 31 or a field strength of about 4.6 × $10^4$V/cm and impinge on an aluminized phosphor screen 26; e.g., P-20, which is deposited as a layer on the output fiber optics face plate 27. The aluminized phosphor prevents visible light feed-back to the photocathode 24. The output phosphor can be any phosphor which emits visible light with wave-length and decay characteristics matched to the particular application desired; i.e., still or moving film recording, direct viewing with or without movement, or use with imaging devices. The output fiber optics face plate 27 again serves as a light pipe and maintains image resolution. It should be noted that both the input and output fiber optics face plate 23 and 27, respectively, also serve as vacuum seals. In addition, the output plate 27 brings the final intensified image to a plane flush with the back surface of the intensifier, thus making the device easy to couple with any form of an image recording device such as cameras, CCD (charge-coupled devices), TV recordings, and the like.

It should also be noted that although the input and output fiber optics face plates are preferred, they are not essential for operation. Thin plane glass may also be used except that it is much more fragile.

The housing 28, as shown, is cylindrical, with all elements also being generally cylindrical. The fiber optics face plates 23, 27 as previously noted, also serve as seals for the housing which contains the photocathode 24, microchannel plate amplifier 25 and phosphor screen 26 in high vacuum. The converter, consisting of the light shield 21 and phosphor or scintillator material 22, covers the radiation input end of the housing. The converter, however, is outside of the housing 28 which contains the evacuated area 29. Pins 32, 33, 34 and 35 protrude from the housing 28 to provide power supply connections to the LIXIscope. Typically, photocathode 24 is at −200V, the input of the microchannel plate amplifier 25 is grounded, the output of the microchannel plate amplifier 25 is between 700 and 1000V and the phosphor screen 26 is between 5KV and 6KV.

Figure 4:
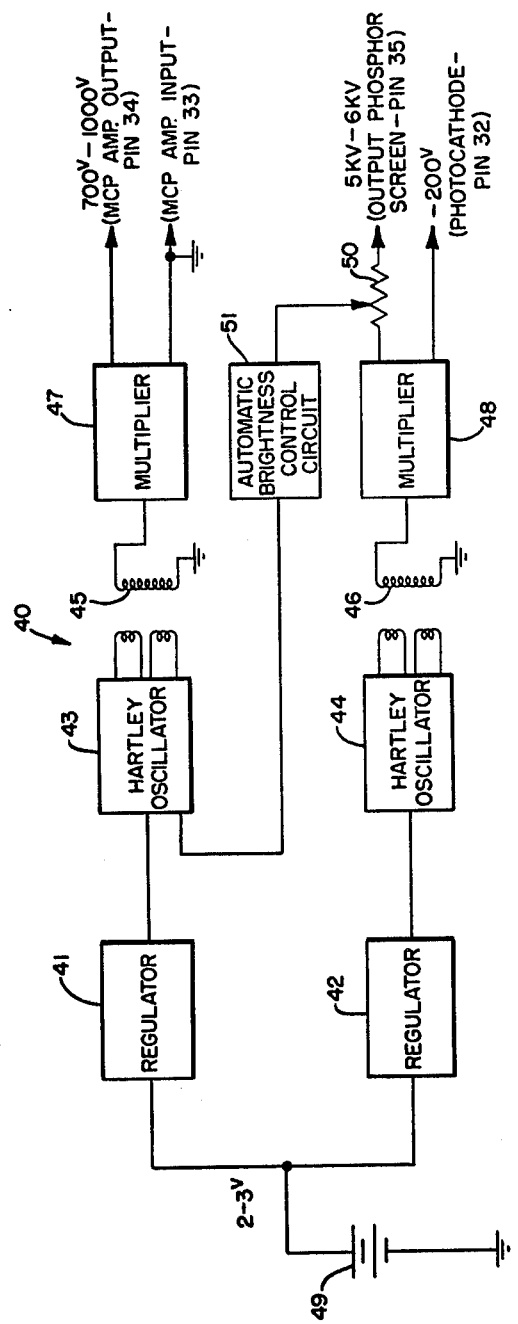
FIG. 4 is a block diagram of a power supply for the present invention.

FIG. 4 depicts a block diagram of a power supply 40 which may be used with the LIXIscope. There are two drive chains consisting of regulators 41, 42, Hartley Oscillators 43, 44, step-up transformers 45, 46, and multipliers 47, 48. The power supply 40 may be powered with a 2.0 to 3.0 volt source 49 which may be made completely portable. Potentiometer 50 is placed in series with the output phosphor screen. Since there is very low current flow the voltage to the screen remains essentially constant. However, the variation of the voltage drop across the potentiometer is fed back to the Hartley Oscillator 43 to change MCP amplifier output. Operationally when the output phosphor screen becomes excessively bright, the drop across the potentiometer 50 becomes relatively large. This drop is fed back via the automatic brightness control circuit 51 to the Harley Oscillator 43 to decrease its output level. This results in lowering the MCP amplifier output voltage which decreases its gain. By lowering the MCP amplifier gain the phosphor is dimmed and the screen thereby protected from burning. The power supply may be encased in silicone rubber or a similar protective material placed around the LIXIscope.

Figure 5:
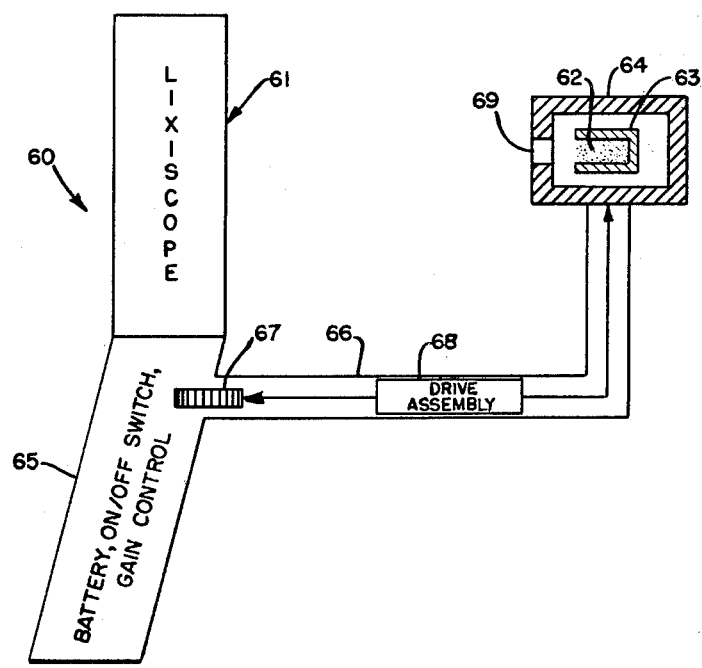
FIG. 5 is a side view of the present invention with the image intensifier mechanically coupled to its own source.

While the LIXIscope may be employed with its attendant advantages with a conventional radiation source turned down to a very low intensity level, it can also be usefully employed with its own small radiation source. This source may be independent of the LIXIscope, or, alternatively, mechanically coupled to the LIXIscope. FIG. 5 depicts the side view of an embodiment 60 of a LIXIscope 61 mechanically coupled to a radiation source 62. As shown the radiation source is a radioactive isotope but it could be a radiation generator. The radiation source 62 is contained in an open ended heavy metal cylinder 63 whose major axis is shown as horizontal, which is covered by a rotatable, cylindrical, heavy metal radiation shield 64, whose major axis is shown as vertical. A handle 65 is provided which may contain a battery, an on/off switch and a gain control for the LIXIscope. The radiation source is maintained in a fixed positon with respect to the LIXIscope by means of a rigid support arm 66. An on/off thumbknob control 67 is provided for controlling the position of the radiation shield 64 via drive assembly 68. On the "on" position of control 67, shield 64 is positioned so that aperture 69 is directly in line with the LIXIscope and the overall system is operative. On the "off" position, the shield 64 is turned to a position whereby the aperture 69, is turned away from the open end of the cylinder 63 and all output radiaition is blocked. This configuration, therefore, is safe for handling since the radiation is unshield only when necessary and the radiation source is always aligned with the LIXIscope when unshielded.

Because of the high quantum gain of the LIXIscope and the concomitant reduction in patient dosage it becomes possible in certain applications such as dental fluoroscopy and radiography to substitute the conventional X-ray machine with radioactive sources such as $I^{125}$ ($t_{\frac{1}{2}}=60$ days), $Cd^{109}$ ($t_{\frac{1}{2}}=1.3$ years) or $Sn^{119m}$ ($t_{\frac{1}{2}}=250$ days). These are examples of sources which emit X-rays in the energy range required for medical and dental applications. Such sources, which are fully compatible with the LIXIscope, are available commercially with activities in the 10–100 mC range with point-source geometry as generally shown in FIG. 5 as element 62.

It should be noted that several state-of-the-art modifications may be made to the LIXIscope as previously described to further improve its performance; e.g., image quality. The modifications may include (1) using a high resolution converter for special applications such as mammography; (2) using photocathodes which have their sensitivity peaked to match the wave length of the high resolution converters; (3) providing output phosphors with various decay times and wave lengths for specific applications and (4) providing various radioactive sources for use with varying applications and which may be matched to a particular LIXIscope configuration.

The LIXIscope, as described above, therefore, has many new features and advantages not found in the prior art. The converters employed have high quantum efficiencies, for instance, in the energy range of medical X-rays. Such high efficiencies and consequently, high information content, are preserved because the radiation impinges directly on the converter without the interference of a window. Concurrently, the high quantum gain of the intensifier is also fully utilized.

The LIXIscope can easily be made in a rugged configuration which is suitable for field and clinical use. This is made possible because the converter is outside the intensifier and yet the intensifier can be operated under a high vacuum without any fragile windows. Moreover, having the converter outside of the intensifier eliminates the problem of contamination of the photocathode by the converter material. Additionally, having the converter outside the intensifier allows for easy change of converters for different applications.

The use of the input and output fiber optics plates eliminates thin and fragile glass windows with no loss in resolution. The flat, input and output surfaces of the LIXIscope allow maximum, and under some applications, direct contact with both the patient and any image recording devices. Obviously, the output image of the LIXIscope may be further intensified by additional intensifiers, magnified or demagnified as deemed necessary. The LIXIscope with its own small radioactive source allows pocket-sized, portable fluoroscopy and radiography with access to previously considered awkward areas. Moreover, the LIXIscope with its own low dosage radiation source can be operated in a fashion limiting unnecessary radiation exposure to other sensitive parts of the body not of diagnostic interest. Because the LIXIscope exhibits such high gain and, therefore, allows use of extremely low intensity sources, long term fluoroscopy, such as with root canal work, can be maintained without exceeding safe dosage limits. Continuous, on-site, and instantaneous visual observation can thus be maintained to observe surgical progress.

The principles, preferred embodiments, and modes of operation of the present invention have been described in the foregoing specifications. The invention which is intended to be protected herein, however, is not to be construed as limited to the particular forms disclosed since these are to be regarded as illustrative rather than restrictive. Variations and changes may be made by those skilled in the art without departing from the spirit of the present invention.

What is claimed is:

1. Apparatus for converting radiation to visible light, comprising:
   means for converting incoming invisible radiation to visible light;
   means for visible light intensification, which means includes a microchannel plate amplifier; and
   means for light coupling said means for converting incoming radiation and said means for visible light intensification.

2. The apparatus of claim 1 wherein said apparatus is mechanically coupled with a radiation source.

3. The apparatus of claim 2 wherein said radiation means is a radioactive souce.

4. The apparatus of claim 2 wherein said radiation means is a radiation generator.

5. The apparatus of claim 2 wherein said radiation source may be made to radiate upon said means for converting incoming radiation.

6. The apparatus of claim 1 wherein said incoming radiation are X-rays.

7. The apparatus of claim 1 wherein said incoming radiation are gamma-rays.

8. The apparatus of claim 1 wherein said incoming radiation are charged particles.

9. The apparatus of claim 1 wherein said incoming radiation are neutral particles.

10. The apparatus of claim 1 wherein said means for converting incoming radiation is mechanically coupled to said means for visible light intensification.

11. The apparatus of claim 1 wherein said means for converting incoming radiation is phosphor.

12. The apparatus of claim 11 wherein said phosphor is one with high efficiency of conversion of X-rays to visible light.

13. The apparatus of claim 11 wherein said phosphor is a rare earth phosphor.

14. The apparatus of claim 11 wherein said phosphor is terbruim activated 90% gadolinuim and 10% lanthanum oxysulfide.

15. The apparatus of claim 1 wherein said means for converting incoming radiation is a scintillator material.

16. The apparatus of claim 15 wherein said scintillator material has a high efficiency of conversion of gamma-rays to visible light.

17. The apparatus of claim 15 wherein said scintillator material is selected from the group consisting of sodium iodide and cesuim iodide.

18. The apparatus of claim 17 wherein said sodium iodide and cesium iodide is impurity activated.

19. The apparatus of claim 15 wherein said scintillator material is plastic.

20. The apparatus of claim 1 wherein said means for converting incoming radiation includes a visible light shield which is transparent to X-ray and gamma-ray radiation.

21. The apparatus of claim 1 wherein said means for visible light intensification is contained in an evacuated area and said means for converting incoming radition is contained outside said evacuated area.

22. The apparatus of claim 1 wherein said means for converting incoming radiation is light coupled to said means for visible light intensification through fiber optics means.

23. The apparatus of claim 22 wherein said means for converting incoming radiation includes a phosphor layer deposit on said fiber optics means.

24. The apparatus of claim 22 wherein said means for converting incoming radiation is mechanically connected to said means for visible light intensification in a mechanically interchangeable fashion.

25. The apparatus of claim 24 wherein said means for converting incoming radiation is a luminescent layer deposited on a fiber optics plate independent of said means for visible light intensification.

26. The apparatus of claim 1 wherein said microchannel plate amplifier is two amplifiers in a chevron configuration.

27. The apparatus of claim 1 wherein said microchannel plate amplifier has curved channels.

28. The apparatus of claim 1 wherein said microchannel plate amplifier has channels with conical inputs.

29. A method of radiation imaging consisting of:
positioning a radiation source before an object and positioning a device behind the object which converts invisible radiation to visible light and subsequently intensifies visible light by means of a light intensifier including a microchannel plate amplifier.

30. The method of claim 29 wherein said radiation source is of low intensity and said device exhibits a high gain.

31. The method of claim 29 wherein said radiation source is an X-ray source.

32. The method of claim 29 wherein said radiation source is a gamma-ray source.

33. The method of claim 29 wherein said radiation source is a charged particle source.

34. The method of claim 29 wherein said radiation source is a neutral particle source.

35. The method of claim 29 wherein said radiation source is radioactive.

36. The method of claim 29 wherein said radiation source is a radiation generator.

37. The method of claim 29 wherein said radiation source is mechanically coupled to said device.

* * * * *